United States Patent
Jess et al.

(10) Patent No.: US 7,369,073 B2
(45) Date of Patent: May 6, 2008

(54) MICROSCOPY SYSTEM AND RECORDING METHOD FOR VISUALIZING FLUORESCENCE

(75) Inventors: Helge Jess, Oberkochen (DE); Petra Weinschenk, Aalen (DE); Martin Schneider, Koenigsbronn (DE); Christoph Hauger, Aalen (DE); Hans-Joachim Miesner, Aalen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 0 days.

(21) Appl. No.: 11/544,269

(22) Filed: Oct. 6, 2006

(65) Prior Publication Data
US 2007/0090985 A1    Apr. 26, 2007

(30) Foreign Application Priority Data
Oct. 6, 2005 (DE) ............ 10 2005 048 006

(51) Int. Cl.
*H03M 1/00* (2006.01)
(52) U.S. Cl. ............ 341/139; 341/155; 348/79; 348/229.1; 348/333.01
(58) Field of Classification Search ............ 341/139
See application file for complete search history.

(56) References Cited

U.S. PATENT DOCUMENTS

| | | | |
|---|---|---|---|
| 4,884,890 A | 12/1989 | Coates | |
| 5,512,947 A * | 4/1996 | Sawachi et al. | 348/243 |
| 5,614,948 A | 3/1997 | Hannah | |
| 5,804,813 A * | 9/1998 | Wang et al. | 250/201.3 |
| 6,059,720 A | 5/2000 | Furusawa et al. | |
| 6,740,868 B1 | 5/2004 | Knebel et al. | |
| 6,876,399 B1 * | 4/2005 | Masuyama et al. | 348/649 |
| 6,917,377 B2 * | 7/2005 | Aizaki et al. | 348/79 |
| 7,053,935 B2 * | 5/2006 | Guimaraes et al. | 348/222.1 |
| 7,199,823 B2 * | 4/2007 | Masuyama | 348/229.1 |
| 7,248,282 B2 * | 7/2007 | Maddison | 348/79 |
| 2001/0043279 A1 * | 11/2001 | Niikawa et al. | 348/345 |
| 2001/0045506 A1 * | 11/2001 | Masuyama | 250/201.3 |
| 2002/0176007 A1 | 11/2002 | Cappellaro | |
| 2003/0016301 A1 * | 1/2003 | Aizaki et al. | 348/345 |

(Continued)

FOREIGN PATENT DOCUMENTS

DE    198 09 727 A1    9/1998

(Continued)

OTHER PUBLICATIONS

European Search Report for EP 06 02 1081 dated Jan. 30, 2007.

(Continued)

*Primary Examiner*—Khai M. Nguyen
(74) *Attorney, Agent, or Firm*—Potomac Patent Group PLLC

(57) ABSTRACT

An image sensor and a circuitry associated with the image sensor is used for recording a series of fluorescence images. The image sensor comprises a plurality of pixels for accumulating charges generated by incident radiation, and the circuitry converts the charges accumulated in the pixels into binary numbers. A gain of the circuitry is adjustable. The gain is set to a suitable maximum value at the beginning of a recording procedure. The gain is reduced if it is determined during the recording procedure that one or more brightness values of the recorded image exceed a suitably chosen maximum brightness value.

20 Claims, 4 Drawing Sheets

U.S. PATENT DOCUMENTS

2003/0098921 A1* 5/2003 Endo .................... 348/345
2004/0109231 A1 6/2004 Haisch et al.

FOREIGN PATENT DOCUMENTS

| DE | 199 57 418 A1 | 5/2001 |
| DE | 101 09 130 A1 | 9/2002 |
| DE | 103 39 784 A1 | 3/2004 |
| DE | 102 52 005 A1 | 5/2004 |
| DE | 699 11 953 T2 | 8/2004 |
| EP | 0 400 605 A2 | 12/1990 |
| WO | WO 1999/057545 | 11/1999 |

OTHER PUBLICATIONS

"Imaging Sensors," Photonics Spectra, Aug. 2005, p. 56.
Holst, G.C., "Cameras," CCD Arrays, Cameras, and Displays, Chapter 5, pp. 146-149, undated.
Data Sheet XC-E Series Sony Video Camera, Sony Corporation, 2000, pp. 1-4.
User's Guide XC-E Series Sony Camera Module, Sony Corporation, 1999, pp. 1-35.
"BE-IR20/21—Infrared B/W Camera Modual Operation Guide,"Hitachi Kokusai Electric Inc., Dec. 27, 2000, pp. 1-21.

* cited by examiner

MICROSCOPY SYSTEM AND RECORDING METHOD FOR VISUALIZING FLUORESCENCE

BACKGROUND OF THE INVENTION

1. Field of the Invention

The present invention relates to a microscopy system and a recording method for visualizing a fluorescence.

2. Brief Description of Related Art

Fluorescent markers are used in medical applications and biological applications for various purposes, such as visualizing certain tissue features, tissue types, tissue structures and tissue functions. Herein, a fluorescent marker or a precursor of such fluorescent marker is applied to a tissue sample or a patient under examination or treatment. The fluorescent marker is accumulated in particular tissue types or tissue structures of the tissue sample or of the patient, and the tissue structures and tissue types can be perceived and localized by an observer by illuminating the tissue sample with light exciting a fluorescence and observing corresponding fluorescent light. Various optical tools are used for making the fluorescent light, which often has a low intensity, visible for the observer. A conventional microscopy system and recording method is known from US 2004/0109231 A1, the entire contents of which are incorporated herein by reference. Using this conventional microscopy system it is possible to apply the fluorescent marker or its precursor to a sample and then to observe a corresponding fluorescence and to record corresponding images, to archive those images and to reproduce those images as a film.

In the conventional system it may happen that recorded images have a low quality, such as a low brightness and a low contrast, and that a significant fluorescence may not be visible in the recorded images. It is then necessary to repeat a detection procedure using a higher concentration of the fluorescent marker or modifying other parameters for obtaining a desired result.

SUMMARY OF THE INVENTION

The present invention has been accomplished taking the above problems into consideration.

Embodiments of the invention provide a microscopy system and a recording method for visualizing a fluorescence in which an occurring fluorescence can be displayed such that it is better visible.

Embodiments of the present invention use an image sensor and circuitry coupled to the image sensor. The image sensor comprises a plurality of pixels for accumulating charges generated by incident radiation, and the circuitry converts the charges accumulated in the pixels into binary numbers using a gain which is adjustable. The gain is set to a suitable maximum value when a recording sequence is started. The gain will be reduced if it is determined, during the recording sequence, that one or more intensity values of a recorded image exceed a suitably chosen brightness value.

By setting the gain to a maximum value at the beginning of the recording, it is ensured that also a weak fluorescence results in a significant image signal. The image brightness of the fluorescence image will continuously increase after application of the fluorescence marker or its precursor. It is then possible that some brightness values exceed the maximum brightness value or represent an even greater brightness value or even an overflow value since the gain was initially set to a high value. To avoid this, the value of the gain is continuously reduced, such that images having a proper contrast and in which regions having brightness values exceeding the maximum value or representing an overflow value remain small. It is possible to record images with high contrast already at the beginning of the fluorescence where detectable fluorescent intensities are low, and to continue to record satisfactory images when the intensity of the fluorescence continuously increases.

An embodiment of the invention provides a recording method for a series of fluorescence images using a camera system, wherein the camera system comprises an image sensor having a plurality of pixels for accumulating charges generated by incident radiation, and circuitry for converting an amount of charges accumulated in groups of pixels into binary numbers wherein a gain of the transformation is adjustable such that each of the binary numbers represents charge amounts within charge amount ranges, wherein charges from within the charge amount ranges are less or equal than a charge amount limit depending on the at least one gain, and wherein the method comprises: setting of the at least one gain such that the charge amount limit is a small first charge amount, and wherein the method then comprises: repeatedly receiving, from the circuitry, binary numbers representing an image detected by the image sensor, re-adjusting the at least one gain such that the charge amount limit is greater than in the preceding adjustment of the at least one gain if at least one of the binary numbers representing the detected image represents a charge amount exceeding a maximum value.

Typically, the binary numbers represent detected intensity values associated with the respective pixels of the image sensor. In a displayed image generated from such binary numbers, those regions appear bright which correspond to pixel regions of the image sensor receiving a high radiation dose, whereas pixel regions of the image sensor receiving a low radiation dose appear as dark regions in the corresponding image. It is, however, also possible that the binary numbers represent the charge amounts generated in the pixels according to a different coding scheme. For example, it is possible that the binary numbers represent inverted brightness, such that pixel regions receiving a high radiation dose appear as dark regions in the corresponding regions of the displayed image, whereas regions of the displayed image having a bright appearance correspond to pixel regions of the image sensor receiving a low radiation dose.

The circuitry converts the charge amount accumulated in a group of pixels into a plurality of binary numbers such that a charge amount range is associated with each binary number, wherein charge amount ranges corresponding to different binary numbers do substantially not overlap. The charge amounts from within the charge amount ranges are less than a charge amount limit. A charge amount accumulated in a group of pixels and greater than the charge amount limit can be converted into a particular binary number representing an overflow. For example, charge amounts can be converted into eight bit binary numbers from zero to 254 and, and the binary number 255 can represent the charge amount limit, or the overflow which is greater than the charge amount limit.

The charge amount limit is determined by the adjustable gain.

The image sensor can be a charged coupler device (CCD) sensor, in which charges accumulated in pixels are shifted out of the sensor in a row direction, wherein charge amounts of each line are serially converted to voltages, wherein the voltages are amplified, and wherein the amplified voltages are converted to binary numbers using an analog-digital-converter (ADC). The amplification of the voltages is achieved by a voltage amplifier having an adjustable gain. Similarly, a gain of the analog-digital-converter can be adjustable.

The image sensor may also comprise a complementary metal-oxide semiconductor (CMOS) sensor in which conversion of a charge amount accumulated in each pixel takes place at a location of the pixel, wherein the voltage values corresponding to the pixels can be read out from the sensor by addressing the row and column of the pixel. Herein it is also possible to adjust a gain of the conversion of the charge amounts into voltages, a gain of amplification of said voltages and also a gain of the conversion of the amplified voltages into binary numbers.

According to an embodiment of the invention, received binary numbers representing an image detected by the image sensor can be recorded in a recording medium.

According to an exemplary embodiment of the invention, the recording in the recording medium is performed only subsequent to a start time, such that plural images detected earlier than the start time will not be recorded.

According to an alternative embodiment, it is possible to record all detected images in the recording medium and to additionally store a marker in the recording medium, wherein the marker indicates a recorded image recorded close to the start time.

The start time can be determined according to plural methods.

According to an embodiment, the start time is determined based on a contrast of the detected images. At a beginning of the recording, when a fluorescent marker has not yet accumulated in the determined sample, a contrast of the recorded fluorescent image will be small or not present. The contrast of the image will increase with increasing accumulation of the fluorescent marker in the sample, and will exceed a lower threshold value. The time at which the lower threshold value is exceeded may then be used as the start time.

The group of pixels from which the accumulated charge amount is converted to a binary number may comprise one single pixel. It is, however, possible that the group of pixels comprises plural pixels.

According to an embodiment, the image sensor may comprise, for example, a CCD sensor in which accumulated charges of four adjacent pixels are combined at the time of reading out the sensor and wherein the combined charges are converted to the binary number.

According to a further embodiment plural binary numbers representing charge amounts of one or more pixels may be averaged such that a plurality of binary numbers, thus representing an intermediate result of the conversion, are combined to a final binary number, resulting in a data reduction will achieving a displayable image which has, compared to a pixel resolution of the image sensor, a reduced resolution, which has, however, reduced image noise.

The fluorescent marker can be any suitable fluorescent marker or precursor thereof. Examples are indocyanine green (ICG) having an excitation wavelength in a region from about 700 nm to about 800 nm and having a fluorescent wavelength in a region from about 800 nm to about 900 nm. A further example of a precursor is 5-aminolevulinic acid (5-ALA) which becomes a fluorescent marker having an excitation wavelength in a range from about 400 nm to about 430 nm and having a fluorescent wavelength in a range from a bout 630 nm to about 720 nm.

BRIEF DESCRIPTION OF THE DRAWINGS

The foregoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

DETAILED DESCRIPTION OF EXEMPLARY EMBODIMENTS

Figure 1:
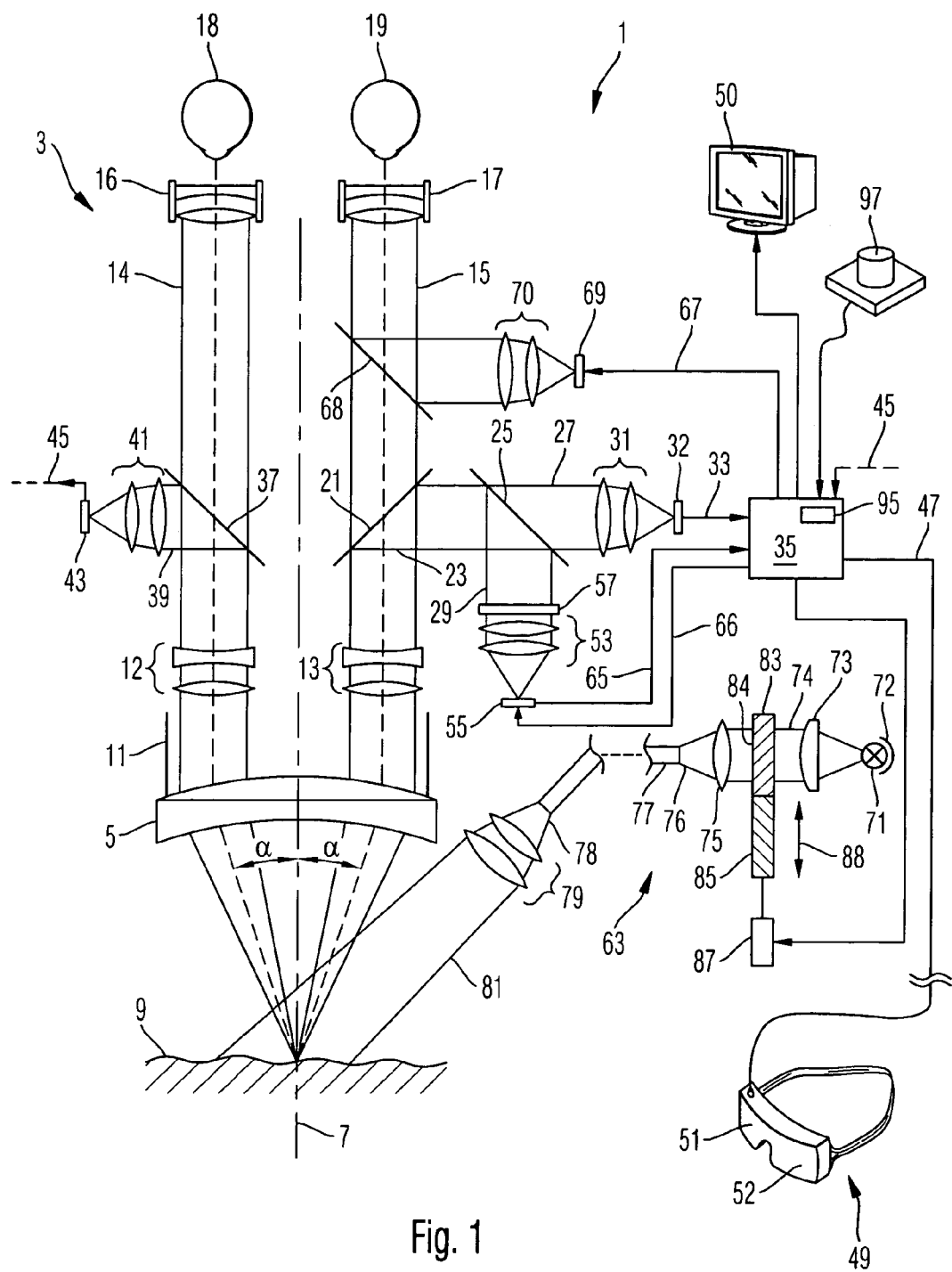
FIG. 1 is a schematic representation of a beam path in a microscopy system according to an embodiment of the present invention.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

FIG. 1 schematically shows a microscopy system 1 comprising a microscopy optics 3 including an objective lens 5 having an optical axis 7. An object 9 to be inspected is disposed in an object plane of objective lens 5. Light emanating from the object 9 is transformed by the objective lens 5 to form a parallel beam 11 in which two zoom systems 12, 13 are disposed at a distance from the optical axis 7. The zoom systems 12, 13 use partial beams 14 and 15 of the parallel beam 11 and supply the partial beams 14, 15 to oculars 16 and 17 through deflecting prisms (not shown in FIG. 1) of a body of a tube of the microscopy system 1. A user may perceive a magnified representation of the object 9 as an image when looking into the oculars 16, 17 with his left eye 18 and right eye 19, respectively. The image perceived with the left eye 18 corresponds to an image when looking onto the object under an angle α with respect to the optical axis, and the image perceived with the right eye 19 corresponds to an image when looking onto the object 9 under an angle –α with respect to the optical axis 7, such that the user perceives a stereoscopic image of the object 9 with his both eyes 18, 19.

A partially transmissive mirror 21 is disposed in the partial beam 15 for branching off a portion of the light thereof as a beam 23. Beam 23 is splitted with a further beam splitter 25 to form beams 27 and 29. Beam 27 is supplied to a light sensitive element of a camera 32 through a camera adapter optics 31 such that the camera 32 detects an image of the object 9 under an observation angle –α with respect to optical axis 7. The images detected with camera 32 are transmitted as image data through a data line 33 to a controller 35.

A beam 39 is branched off from partial beam 14 by a partially transmissive mirror 37. Beam 39 is supplied to a light sensitive element of a further camera 43 through a camera adapter optics 41 such that camera 43 detects images of the object 9 under an observation angle α with respect to the optical axis 7. The images detected by camera 43 are supplied as image data to controller 35 through a data line 45. The controller transmits the images detected by cameras 32, 43 as image data through a line 47 to a head mounted display 49 which is carried by a user of the microscopy system 1 at his head such that integrated displays of the head mounted display 49 which are schematically indicated with reference numerals 51 and 52 in FIG. 1 provide respective images which may be perceived by the user with his left and right eyes, respectively.

Thus, a user who is not in a position of directly looking into the oculars 16, 17 may also perceive a stereoscopic representation of the object 9 by using the head mounted display 49 by observing representations of visible light images of object 9.

Beam 29 is supplied to a light sensitive element of a camera 55 through a camera adapter optics 53 such that camera 55 may detect an infrared image of the object. A filter 57 is disposed in beam 29. A transmission characteristic of filter 57 is adapted to the fluorescence wavelength of the fluorescent marker used in the particular application. In the illustrated example, the fluorescent marker is ICG having a fluorescent emission at about 835 nm. The transmission characteristics of the filter 57 is designed such that only light having a wavelength above 810 nm is transmitted and wherein light below the wavelength of 810 nm is not transmitted. The camera 55 thus detects images of the object 9 which represent a distribution of the fluorescent substance within the object 9, provided that the fluorescence of the substance is excited with an illumination system 63 of the microscopy system 1 as further illustrated below.

The images detected with camera 55 are transmitted through a data line 65 to the controller 35. The controller 35 transmits the images detected with camera 55 as image data through a data line 67 to a LCD display 69. LCD display 69 represents the image data as an image which is superimposed with partial beam 15 by a collimating optics 70 and a partially transmissive mirror 68. The image of the display 69 may be perceived by the eye 19 of the user in superposition with the direct optical image of the object 9. The LCD display 69 represents the infrared light intensity distribution detected by camera 55 in a visible color such as green color. Green color may be advantageously used for representing the infrared image since human tissue forming the object 9 usually comprises green color in a relatively low amount.

The controller performs a data processing of the image data transmitted to display 51 of head mounted display 49 such that the display 51 displays the infrared light images detected by camera 55 superimposed with the visible light images detected by camera 32. Thus, the user wearing the display 49 at his head may also perceive with his right eye a superimposed representation of visible light images and infrared light images of the object.

Even though it is not illustrated in FIG. 1 for ease of reference and clarity, a further beam may be branched off from partial beam 14 supplied to the left eye 18. Such further beam may be supplied to a further infrared camera for generating images which are superimposed with the partial beam 14 of visible light as illustrated above for partial beam 15, LCD display 69, collimating optics 70 and partially transmissive mirror 68. The user will then perceive a stereoscopic infrared light image of the object 9. Image data generated by such additional camera may also be supplied to display 52 of head mounted display 49 such that also head mounted display 49 provides a stereoscopic representation of a distribution of the fluorescent substance within the object 9.

The illumination system 63 comprises a halogen lamp 71 as a light source, a reflector 72 and a collimator 73, for generating a collimated light beam 74 which is directed through one or plural lenses 75 onto an entrance end 76 of an optical fiber bundle 77 for coupling light emitted from light source 71 into the fiber bundle 77. The light is transported by fiber bundle 77 to a position close to the objective lens 5 and emanates from an exit end 78 of the fiber bundle 77. A collimating optics 79 is provided for shaping the emanating light to form an illuminating light beam 81 directed to object 9. The embodiment is not limited to using a halogen lamp as a light source. Also other light sources, such as a xenon lamp, may be used.

The illuminating system 63 further comprises a filter plate 83 having two filters 84 and 85 disposed adjacent to each other. An actuator 87 controlled by controller 35 is provided for displacing the filter plate 83 in a direction indicated by double arrow 88 in FIG. 1 such that filter 84 is disposed in beam 74 in a first position of plate 83 and that filter 85 is disposed in beam 74 in a second position of plate 83.

A transmission characteristics of filter 84 is designed such that filter 84 transmits visible light and light with wavelengths up to an edge at about 800 nm substantially completely, and that wavelengths above the edge are substantially not transmitted. Filter 84 is positioned in beam 74 in applications for observing the fluorescence of the fluorescent substance in the inspected object region 9. The edge at 800 nm is at a wavelength higher than the excitation wavelength of ICG such that light beam 81 both excites the fluorescence detected by camera 55, and illuminates the object region with visible light such that the visible light image of the object may be perceived by looking into the oculars 16, 17 and by observing the images detected by cameras 32, 43. However, the edge at 800 is below the emission wavelength of the fluorescent marker at 835 nm, such that the object is not illuminated with light having a wavelength of the fluorescent light, resulting in that light detected by camera 55 having a wavelength of the fluorescent light only originates from the fluorescence of the fluorescent marker.

When it is not desired to observe the fluorescence, the controller 35 drives the actuator 87 to displace filter plate 83 such that filter 85 is disposed in beam 74. A transmission characteristics of filter 85 is designed such that filter 85 substantially transmits visible light up to an edge and that the filter is substantially non-transmissive for light at wavelengths above the edge at about 710 nm. The filter 85 is used as a thermal protective filter for eliminating radiation from the illuminating light beam 81 which would otherwise result in an unnecessary heating of the object 9. The flank 93 is well below the maximum excitation wavelength 59 of ICG even though an excitation spectrum of ICG also extends to wavelengths below 710 nm. However, a fluorescence of the substance is substantially not excited when filter 85 is disposed in beam 74.

Figure 2:
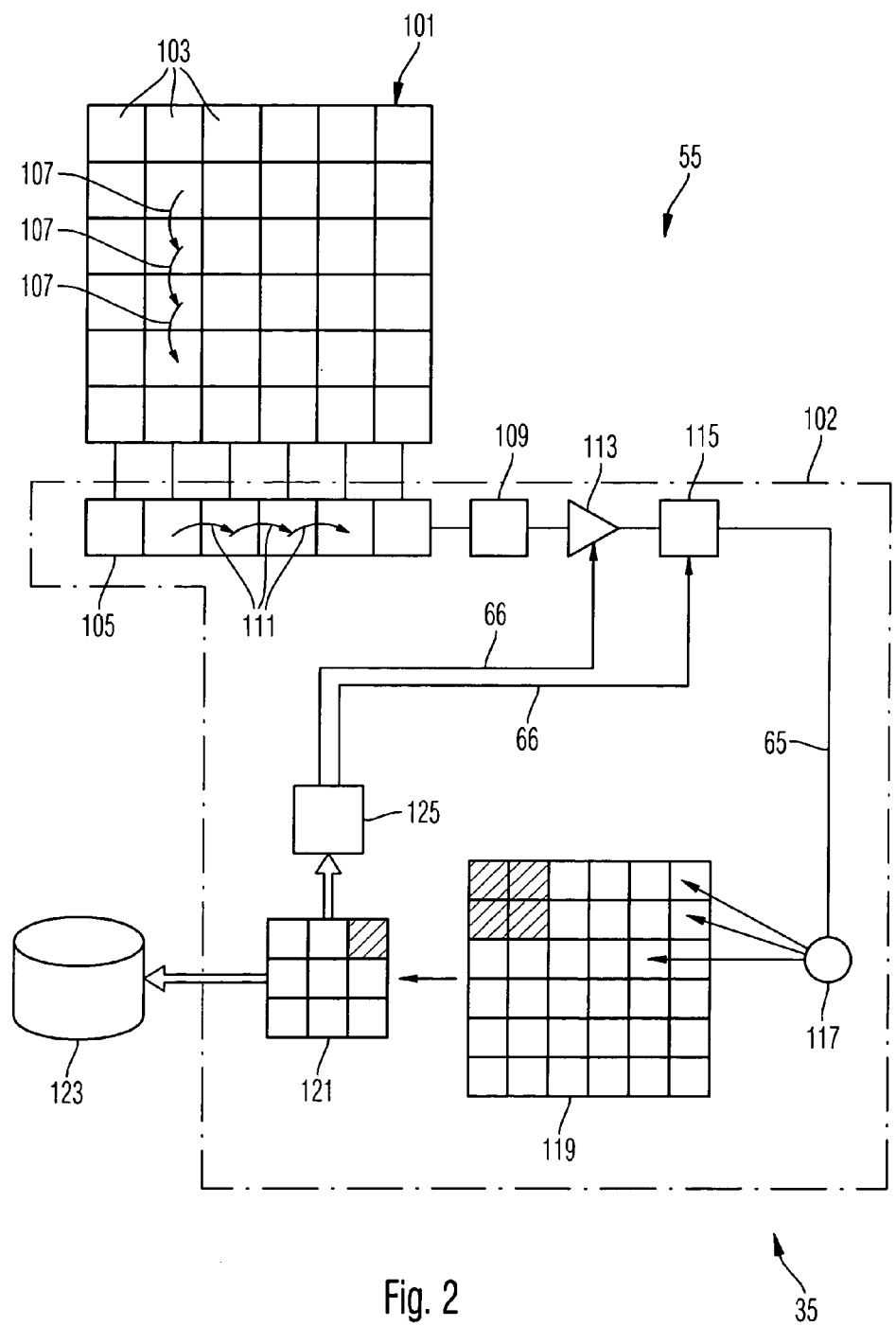
FIG. 2 is a functional diagram of an image sensor and corresponding circuitry as it can be used in the microscopy system shown in FIG. 1.

FIG. 2 illustrates a function of camera 55 and controller 35. The camera 55 is a CCD camera and comprises an image sensor 101 having a plurality of pixels 103 disposed in rows and columns. A readout circuit 102 is used for controlling the sensor 101 and for generating images from the signals of the sensor 101. The readout circuit 102 comprises components which may be disposed at the camera 55 and components which may be disposed at the controller 35.

Charges are accumulated in the pixels during the exposure. At an end of each exposure, the charges accumulated in the respective pixels are transferred line by line to a register 105 as indicated by arrows 107 in FIG. 2. As soon as one line of charges is transferred to register 105, the respective charges are serially transferred to a charge-to-voltage conversion unit 109 as indicated by arrows 101 in FIG. 2. The charge-to-voltage conversion unit 109 converts the respective charges into corresponding voltages which are amplified by an amplifier 113 having variable gain. The voltages are supplied to an analog-digital-converter 115 which also has a variable gain. The analog-digital-converter 115 converts the voltages to binary values. In the illustrated example, the binary values have eight bits, such that brightness values from zero to 254 can be generated. The binary value 255 represents an overflow which means a charge accumulated in a pixel, which charge is greater than a charge amount limit. The charge amount limit is defined by the settings of the gain of the amplifier 113 and by the gain of the analog-digital-converter 115. The combined gains provide a scale factor of the conversion of the charge amount of the pixel to the binary value. The total gain of the conversion can be defined as the amount of electrons accumulated in the pixel divided by the binary number, i.e. the brightness value of the pixel.

The binary numbers are supplied to the controller 35 via a line 65, wherein the controller 35 comprises for example a frame grabber 117 for storing the binary numbers in an intermediate image data memory 119. A processor of the controller 35 then performs a first image processing for reducing an amount of data of the image by filling an image data memory 121 with image data in which each data value represents an image brightness obtained by averaging four corresponding image brightness values of image memory 119, in the illustrated example. In other examples, a stronger reduction of data may be obtained by averaging nine or sixteen or more image brightness values of memory 119 for obtaining one data value in image memory 121. The data reduction also results in that small details and image noise will not influence subsequent calculations.

The image data from memory 121 are written one after the other, i.e. image by image, to a storage medium, such as a hard disk 123. An image analysis module 125 which may be implemented as a piece of software running on a processor of controller 35, performs a brightness analysis of the brightness value stored in memory 121. If one of the brightness values exceeds a maximum value, which is chosen to be 250 in the illustrated example, this indicates that an even brighter subsequent image could exceed the available dynamic range of the binary representation of the image. The image analysis module 125 will then reduce the setting of one or both of the gains of the amplifier 113 and of the analog-digital-converter 115 through control lines 66. For example, the gain is set to a value of 95% of the current gain.

Since the gain is set to a predetermined maximum value at the beginning of the procedure, it is ensured that already weak fluorescences in the images exploit the available dynamic range of the binary coding as far as possible. Thereafter, an overflow in some or more pixels will be avoided as far as possible since the gains are reduced with increasing intensities of the fluorescence images.

It is also assumed herein, that the fluorescence radiation typically has a low intensity which is not easily detected. For this reason, possible reductions of the detected fluorescence intensity are avoided at the beginning of the procedure. Apertures which are eventually present in the optics are removed or opened as far as possible. Further, an exposure time of the camera 55 is adjusted to a predetermined value which is, in particular, a maximum value available and allowed by the camera.

Figure 3:
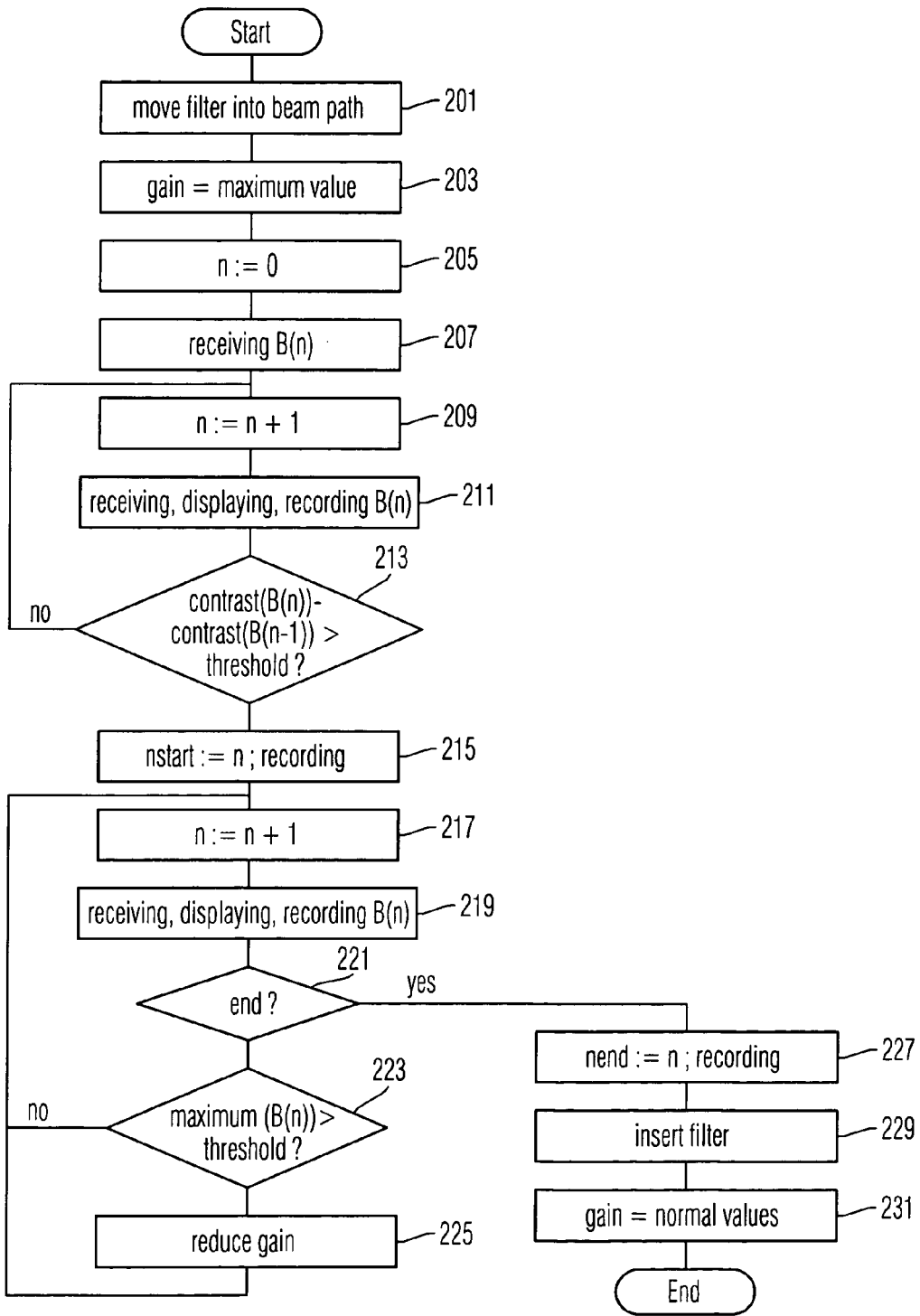
FIG. 3 is a flow diagram for illustrating an image recording method according to an embodiment of the invention.

Reference is made to FIG. 3 for illustrating an embodiment of a recording method for a series of fluorescence images. The procedure illustrated in FIG. 3 can be started, for example, by hitting a button 97 shown in FIG. 1. Thereafter, the controller 35 moves filter 83 into the beam path in a step 201. In a step 203, the gains of the amplifier 113 and of the analog-digital-converter 115 are set to their respective maximum values. An image counter n is set to zero in a step 205, and binary values or brightness values of one image are supplied from the camera through line 65 and stored in the image memory 121, in a step 207.

Thereafter, the image counter is incremented in a step 209, and a next image is received from the camera in a step 211, stored on the hard disk 123 and displayed by the displays 69 and 51, 52, in a step 211. In a step 213 it is determined whether a fluorescence is detectable in the image. This is achieved by comparing a contrast of the currently recorded image with the contrast of the preceding recorded image. If an increase in contrast is detected, a begin of the fluorescence is assumed. If this is not the case, the processing is continued with step 209 to repeatedly record images.

The contrast in an image can be determined by subtracting the smallest brightness value in the image from the highest brightness value in the image. The resulting difference is indicative of the contrast.

If a change in contrast greater than a predetermined threshold is detected in step 213, the start of the fluorescence is concluded, and the processing is continued at a step 215 in which the current value of the image counter n is stored as nstart.

Thereafter, the image counter n is incremented in a step 217, and a next image is received, displayed and recorded in a step 219. In a step 221, it is determined whether the processing should be terminated. Such termination may include to determine whether a maximum duration, such as 300 seconds is exceeded, or a state of a user interface element, such as button 97 may be determined which allows a user to terminate recording of further images.

It is further possible to determine the termination of the recording by performing an image analysis in step 221. The image analysis may, for example, determine whether a fluorescence fades away, which can be achieved by determining whether maximum brightness values of the image fall below a suitably set threshold value.

If it is intended to record only an increase of the fluorescence intensity in a series of images, an end of the fluorescence may be determined by comparing brightnesses of subsequent images. If an increase in brightness is no longer determined, the controller 35 may terminate the recording of further images in a step 221 and continue the processing at a step 227.

If the end of the processing is not reached, it is determined in a step 223 whether the brightness of an image value exceeds a threshold value. As illustrated above with reference to FIG. 2, the threshold value is chosen to be 250, considering that a greatest number which can be represented with eight bits is 255. If the determination in step 223 results in that the maximum brightness is not reached, the processing is continued at step 217 for recording, displaying and storing further images. If the maximum brightness is reached, processing is continued at a step 225, in which the gain of the amplifier 113 and/or the gain of the analog-digital-converter 115 is reduced by e.g. 5%. Thereafter processing is continued at step 217, for recording, displaying and storing further images and for further reducing the gains, if necessary.

If the end of the recording is reached in step 221, processing is continued at step 227, in which the current value of the image counter is stored as nend. Thereafter, the fluorescence filter 83 is removed from the beam path, and the heat protective filter 85 is inserted in the beam path in a step 229. Thereafter, the gain of the amplifier 113 and the gain of the analog-digital-converter 115 are set to normal values as used in a mode of normal operation of the camera in a step 231.

Figure 4:
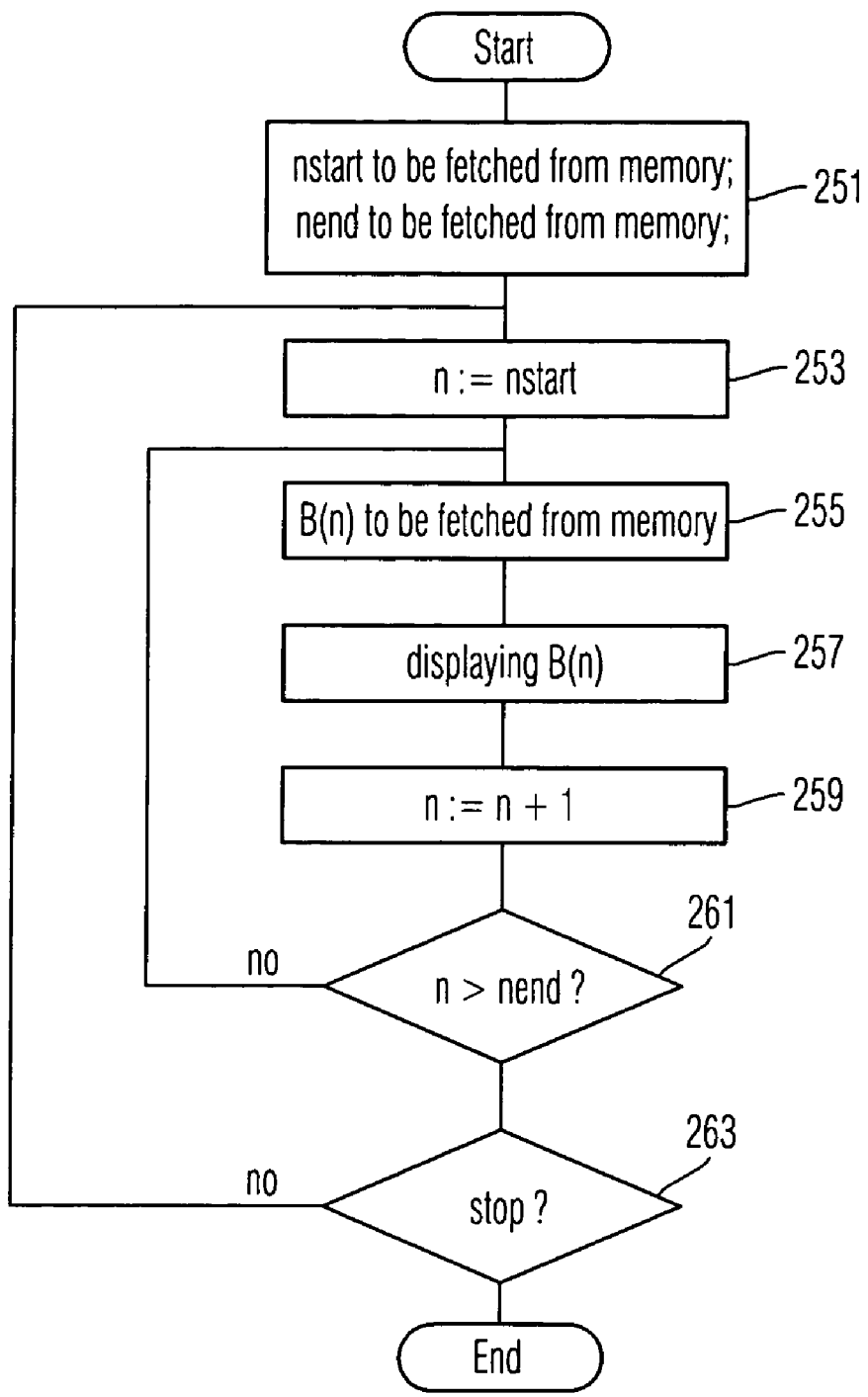
FIG. 4 is a flow diagram for illustrating an image display method.

Reference is now made to the flow diagram shown in FIG. 4 for illustrating a procedure for reproducing the fluorescence images.

After starting the reproduction, the images stored in the storage medium 123 are displayed on the displays 69 and 49 or on a monitor 50 connected to the controller 35. For this purpose, the values nstart and nend representing the start and the end of the recording are fetched from the memory in a step 251. Thereafter, the image counter n is set to the start value nstart in a step 253. The image B(n) corresponding to the image counter n is fetched from the storage medium 123 in a step 255 and displayed on the various displays in a step 257. The image counter is incremented in a step 259. If the image counter has not reached the value nend in a determination performed in a step 261, processing is continued at step 255 for fetching further images from the storage medium and displaying these images. If it is determined in step 261 that all images have been displayed, it is determined in a step 263 whether the user has terminated the procedure. If this is not the case, processing is continued at step 253, for reproducing the series of images again.

As illustrated above, it is possible to reduce the gain as soon as a maximum image intensity exceeds the threshold. It is, however, also possible to increase the gain again as soon as the greatest brightness values in the images fall below a further threshold value. This allows to continue recording images using the available dynamic range also when a fluorescence decreases.

The images can be stored in the storage medium using any data format. It is in particular possible to store the image in a compressed data format, wherein any suitable data compression method can be used to reduce the amount of data to be stored. For example, a MPEG method can be used for compressing the video images, wherein only a portion of the images is stored as a complete image and wherein remaining image are stored as difference values, predictive values and motion vectors such that they can be recalculated from the stored data. It is apparent that the compression of the image data may also result in a certain reduction of image quality, wherein such reduction will not result in a significant deterioration of the performance of the illustrated microscopy system and method in practice.

It is further possible to store the gain or a value representing the gain of the amplifier 113 and/or the analog-digital-converter 115 at the time of detection of an image together with the image data in the storage medium. It is then possible to take account of the gain used for recording an image at the time of reproduction. For example, an image recorded at a relatively high gain may be reduced at a reduced brightness as compared to an image recorded at a relatively lower gain. Herewith it is possible to allow a user to better perceive an intensity of a fluorescence increasing with time. In particular, the user may switch between two reproduction modes, wherein, in a first reproduction mode, images are reproduced while taking account of the gain at the time of recording of the images, while such adaptation is not performed in a second mode of reproduction in which the images are reproduced substantially as recorded.

According to embodiments, an image sensor and a circuitry associated with the image sensor is used for recording a series of fluorescence images. The image sensor comprises a plurality of pixels for accumulating charges generated by incident radiation, and the circuitry converts the charges accumulated in the pixels into binary numbers. A gain of the circuitry is adjustable. The gain is set to a suitable maximum value at the beginning of a recording procedure. The gain is reduced if it is determined during the recording procedure that one or more brightness values of the recorded image exceed a suitably chosen maximum brightness value.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. A microscopy system for visualizing a fluorescence, wherein the microscopy system comprises:
   an image sensor having a plurality of pixels for accumulating charges generated by incident radiation;
   microscopy optics having a first beam path for imaging an object region onto the pixels of the image sensor;
   circuitry for converting a charge amount accumulated in a group of pixels into binary numbers, wherein at least one gain of the conversion is adjustable such that each binary number represents a charge amount from within a range of charge amounts less than a charge amount limit dependent on the at least one gain; and
   a controller which is configured to
   adjusting the at least one gain such that the charge amount limit is a small first charge amount; and
   then repeatedly receiving binary numbers representing an image detected by the image sensor from the circuitry and adjusting the at least one gain such that the charge amount limit is greater than in the preceding adjusting of the at least one gain if at least one of the binary numbers representing the detected image represents a charge amount greater than the maximum value.

2. The microscopy system according to claim 1, further comprising a recording medium, wherein the controller is further configured to store the binary numbers representing the image detected by the image sensor in the recording medium.

3. The microscopy system according to claim 2, wherein the controller is further configured to store the binary numbers in the recording medium only after a start time.

4. The microscopy system according to claim 1, further comprising a display for displaying the images represented by the binary numbers.

5. The microscopy system according to claim 1, wherein the microscopy optics comprises a second beam path including at least one ocular for displaying the object region to an eye of a user.

6. The microscopy system according to claim 1, wherein the image sensor comprises one of a charge coupled device (CCD) sensor and a complementary metal-oxide semiconductor (CMOS) sensor.

7. The microscopy system according to claim 1, wherein the circuitry comprises an analog amplifier, and wherein the at least one gain is a gain of the analog amplifier.

8. The microscopy system according to claim 1, wherein the circuitry comprises an analog-digital-converter and wherein the at least one gain is a gain of the analog digital converter.

9. The microscopy system according to claim 1, wherein the maximum value represents a threshold charge amount associated with saturation effects including an overflow charge of at least one pixel.

10. A recording method for a series of fluorescence images using a camera system, wherein the camera system comprises:
- an image sensor having a plurality of pixels for accumulating charges generated by incident radiation;
- circuitry for converting a charge amount accumulated in a group of pixels into binary numbers, wherein at least one gain of the conversion is adjustable such that each binary number represents a charge amount from within a range of charge amounts less than a charge amount limit dependent on the at least one gain; and
- wherein the method comprises:
- adjusting the at least one gain such that the charge amount limit is a small first charge amount; and
- wherein the method then repeatedly comprises:
- receiving binary numbers representing an image detected by the image sensor from the circuitry; and
- re-adjusting the at least one gain such that the charge amount limit is greater than in the preceding adjusting of the at least one gain if at least one of the binary numbers representing the detected image represents a charge amount greater than the maximum value.

11. The method according to claim 10, wherein the receiving of the binary numbers representing the image detected by the image sensor comprises storing of the binary numbers in the recording medium.

12. The method according to claim 11, wherein the binary numbers are stored in the recording medium only after a start time.

13. The recording method according to claim 12, wherein the storing of the binary numbers within the recording medium comprises storing of a first marker representing a start time, and wherein the displaying is performed only for images stored after the start time.

14. The recording method according to claim 11, further comprising
receiving the binary numbers from the recording medium and
displaying the images represented by the binary numbers.

15. The recording method according to claim 12, further comprising determining the start time in dependence of a contrast of the image represented by the binary numbers.

16. The recording method according to claim 10, wherein the group of pixels comprises one single pixel.

17. The recording method according to claim 10, further comprising
applying a fluorescent marker or a precursor of a fluorescent marker to an object, wherein the radiation incident on the image sensor comprises fluorescent radiation emitted from the object.

18. The recording method according to claim 17, wherein the object is a in vitro sample outside a living organism.

19. The recording method according to claim 17, wherein the object is a portion of an animal or human body.

20. The recording method according to claim 10, wherein the maximum value represents a threshold charge amount associated with saturation effects including an overflow charge of at least one pixel.

* * * * *